US009801920B2

(12) United States Patent
Kim et al.

(10) Patent No.: US 9,801,920 B2
(45) Date of Patent: Oct. 31, 2017

(54) **ANTIMICROBIAL COMPOSITION COMPRISING *FILOBASIDIUM*-SUPPRESSING AGENT DERIVED FROM NATURAL SUBSTANCE**

(71) Applicant: CHUNG-ANG UNIVERSITY INDUSTRY-ACADEMIC COOPERATION FOUNDATION, Seoul (KR)

(72) Inventors: Won Yong Kim, Seoul (KR); Sang Gue Park, Goyang-si (KR); Hee Kuk Park, Gwangmyeong-si (KR)

(73) Assignee: Chung-Ang Univ Industry-Academic Coop. Foundation, Seoul (KR)

( * ) Notice: Subject to any disclaimer, the term of this patent is extended or adjusted under 35 U.S.C. 154(b) by 192 days.

(21) Appl. No.: 14/419,476

(22) PCT Filed: May 6, 2013

(86) PCT No.: PCT/KR2013/003926
§ 371 (c)(1),
(2) Date: Feb. 3, 2015

(87) PCT Pub. No.: WO2014/021540
PCT Pub. Date: Feb. 6, 2014

(65) Prior Publication Data
US 2015/0216922 A1    Aug. 6, 2015

(30) Foreign Application Priority Data
Aug. 3, 2012   (KR) ........................ 10-2012-0085259

(51) Int. Cl.
| | |
|---|---|
| A61K 36/00 | (2006.01) |
| A61K 36/75 | (2006.01) |
| A61K 36/78 | (2006.01) |
| A61K 36/744 | (2006.01) |
| A61K 8/97 | (2017.01) |
| A61K 36/185 | (2006.01) |
| A61K 36/42 | (2006.01) |
| A61Q 5/00 | (2006.01) |
| A61Q 17/00 | (2006.01) |
| A61K 36/31 | (2006.01) |

(52) U.S. Cl.
CPC ................ *A61K 36/75* (2013.01); *A61K 8/97* (2013.01); *A61K 36/185* (2013.01); *A61K 36/31* (2013.01); *A61K 36/42* (2013.01); *A61K 36/744* (2013.01); *A61K 36/78* (2013.01); *A61Q 5/006* (2013.01); *A61Q 17/005* (2013.01); *A61K 2800/59* (2013.01)

(58) Field of Classification Search
CPC ..................................................... A61K 36/00
See application file for complete search history.

(56) References Cited

U.S. PATENT DOCUMENTS

| | | | |
|---|---|---|---|
| 2002/0172648 A1 | 11/2002 | Hehner et al. | |
| 2008/0009802 A1* | 1/2008 | Lambino ........... | A61M 37/0015 604/173 |
| 2010/0209368 A1* | 8/2010 | Walsh ............................ | 424/59 |
| 2012/0058057 A1* | 3/2012 | Pitner .................... | A61Q 5/006 424/45 |

FOREIGN PATENT DOCUMENTS

| | | | |
|---|---|---|---|
| CN | 101152410 A | * | 4/2008 |
| CN | 101342359 A | | 1/2009 |
| CN | 101716291 A | | 6/2010 |
| CN | 102038922 A | | 5/2011 |
| CN | 102210842 A | | 10/2011 |
| JP | 61-238717 A | | 10/1986 |
| JP | 64-38011 A | | 2/1989 |
| JP | 2-48514 A | | 2/1990 |
| JP | 3-176413 A | | 7/1991 |
| JP | 4-5222 A | | 1/1992 |
| JP | 10-182346 A | | 7/1998 |
| JP | 11255625 A | * | 9/1999 |
| JP | 2000-7574 A | | 1/2000 |
| JP | 2001-288047 A | | 10/2001 |
| JP | 2006-124355 A | | 5/2006 |
| JP | 2008-37764 A | | 2/2008 |
| KR | 10-2002-0092340 A | | 12/2002 |
| KR | 2003020908 A | * | 3/2003 |
| KR | 10-2004-0001441 A | | 1/2004 |
| KR | 10-2006-0034155 A | | 4/2006 |
| KR | 2007070717 A | * | 7/2007 |
| KR | 10-2009-0094617 A | | 9/2009 |
| KR | 10-1017709 B1 | | 2/2011 |
| KR | 10-2012-0067804 A | | 6/2012 |
| KR | 20120067804 A | * | 6/2012 |
| WO | 2012/033422 A1 | | 3/2012 |

OTHER PUBLICATIONS

Database WPI Week 201254 Thomson Scientific, London, GB; AN 2012-H70714, XP002754721, & KR 2012 0067804 A (Han Bang Myeongga Co Ltd) Jun. 26, 2012 (Jun. 26, 2012)—2 pages.
Database WPI Week 200819 Thomson Scientific, London, GB; AN 2008-054882, XP002754722 & JP 2008 037764 A (Shiseido Co Ltd) Feb. 21, 2008 (Feb. 21, 2008)—2 pages.
Database WPI Week 201206 Thomson Scientific, London, GB; AN 2011-P10291, XP002754723 & CN 102 210 842 A (Liu M) Oct. 12, 2011 (Oct. 12, 2011)—2 pages.
Extended European Search Report dated Mar. 7, 2016 of corresponding European Patent Application No. 13825689.6—9 pages.

(Continued)

*Primary Examiner* — Qiuwen Mi
(74) *Attorney, Agent, or Firm* — Knobbe Martens Olson & Bear LLP

(57) ABSTRACT

The present invention relates to an antimicrobial composition derived from a natural substance. Since the composition effectively suppresses *Filobasidium*, an organism that has been newly identified as causing dandruff, the present invention can effectively prevent and/or treat seborrhoeic dermatitis and dandruff. Also, since the antimicrobial composition of the present invention includes a natural substance as an active ingredient, little consumer aversion will result. Also, it is expected that the antimicrobial composition of the present invention can be used for developing an antidandruff agent having a reduced content of materials which are typically used as antidandruff agents and the safety of which is questionable.

9 Claims, 1 Drawing Sheet

(56) References Cited

OTHER PUBLICATIONS

Konishi et al., "Sensitivity of Propionibacterium acnes against Kampo extract formulations", Science of Kampo Medicine 7, 1986, vol. 10, No. 7, pp. 14-20 and its summary English translation in 2 pages.
Yang et al., "Study on the extraction technology and antimicrobial activity of polysaccharide from *Capsella brusa-pastoris* L.", Shipin Gongye Keji(Science and Technology of Food Industry), 2010, vol. 31, No. 4, pp. 146-148,151.
Selenu et al., "Phytochemical study on *Capsella bursa pastoris* L", Bollettino chimico farmaceutico, 2005, vol. 1, 44, No. 1, pp. 66-78.
El-Abyad et al., "Preliminary screening of some Egyptian weeds for antimicrobial activity", Microbios, 1990, vol. 62, pp. 47-57.
Park, Hee Kuk et al., "Characterization of the Fungal Microbiota (Mycobiome) in Healthy and Dandruff-Afflicted Human Scalps", PloS ONE, Feb. 29, 2012, vol. 7, Issue 2, pp. 1-6.
International Search Report dated Aug. 12, 2013 of PCT/KR2013/003926 which is the parent application and its English translation—4 pages.
Nielsen N. H., et al., "Allergic contact dermatitis caused by zinc pyrithione associated with pustular psoriasis", American Journal of Contact Dermatitis, Sep. 1997, vol. 8, Issue 3, Abstract.
Cosmetic and Toiletries, Dec. 1987, vol. 102, No. 12—4 pages.
Park et al., "Clinical Efficacy for 1% Zinc Pyrithione Shampoo for the Treatment of Dandruff", Korean Journal Dermatol, 2009, vol. 47, p. 875-876.
Office Action dated Oct. 27, 2013 of corresponding Korean Patent Application No. 10-2012-0085259—4 pages.

\* cited by examiner

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 1
gcatatcaat aagcggagga aaag                24

<210> SEQ ID NO 2
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 2
ggtccgtgtt tcaagacgc                19

ANTIMICROBIAL COMPOSITION COMPRISING *FILOBASIDIUM*-SUPPRESSING AGENT DERIVED FROM NATURAL SUBSTANCE

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 24964593_1.TXT, the date of creation of the ASCII text file is Jan. 6, 2017, and the size of the ASCII text file is 906 bytes.

TECHNICAL FIELD

The present invention relates to an antimicrobial composition derived from a natural substance, and more specifically, to a composition for preventing or treating dandruff, which is derived from a natural substance and has an effect of suppressing *Filobasidium* sp. which is a fungus that has been newly identified as causing dandruff.

BACKGROUND ART

Seborrhoeic dermatitis is a chronic inflammatory skin disease which occurred in the scalp and face in which sebaceous glands are highly abundant, particularly, eyebrows, a nose, lips, ears, armpits, chests, the groin, and the like. In this case, a condition whose symptoms appear slightly on the scalp is referred to as 'dandruff.'

Dandruff means that dead or scaly cells of the scalp formed by active metabolism of the human body are desquamated in the form of horny mass, which is formed when the cells are caked with secretions from the sebaceous glands of the scalp.

In a histological aspect of dandruff, new cells are formed in the stratum basale of the scalp epidermis, and pushed up. When the cells pushed up to the uppermost layer of the stratum corneum, the cells are desquamated. In this case, the old cells barked off become dandruff. Approximately one month is generally required until the cells are formed and desquamated, which is referred to a turn-over of the cells. An amount of dandruff increases as such a turn-over cycle is shortened, and ichtyosis is caused by secretion and accumulation of sebum due to dysfunction in secretion of lipids from sebaceous glands, living habits or stress, abnormalities in environments such as ambient temperature or moisture, or abnormalities in hormones, depending on the individual difference, sex, age, etc. As a result, a turn-over cycle of epidermal cells is shortened by stimulants such as free fatty acids generated when skin fungal flora or fungi of the skin fungal flora decompose triglycerides in lipids, the stratum corneum gets thick and hyperkeratosis appears since the cell divisions in the stratum corneum more actively occur than those of normal persons, scales are observed with the naked eye, the infiltration of inflammatory cells occurs, and inflammatory findings are partially observed.

The term "ichtyosis" refers to a condition in which an amount of such dandruff increases to a level at which the dandruff is observed with the naked eye. In numerous cases, the ichtyosis easily recurs, and is accompanied by pruritus. When ichtyosis develops, the scalp is excessively rubbed due to dandruff or itching, resulting in damaged scalp. In some cases, the ichtyosis may cause inflammation in the scalp, or often becomes a cause of hair loss. Therefore, dandruff is a kind of seborrhoeic dermatitis which develops in the scalp, and is known to be a symptom developing when secretions of sebaceous glands, secretions of sweat glands, keratinizing materials of the outer skin layer, and the like are generated and accumulated, and infected with microorganisms. Generally, dandruff is characterized in that it often occurs in the face, head, armpit, pubes, and the like, in which the sebaceous glands are functioning actively, and develops immediately after the birth or during puberty.

In recent studies, it is known that skin fungal flora (i.e., dandruff-causing organisms) is deeply associated with the occurrence of dandruff, and yeast has been currently identified as causing dandruff. Among these, Eumycetes (yeasts) referred to as *Pityrosporum ovale* or *Malassezia furfur* are found to be associated with the occurrence of dandruff, and thus interest in the Eumycetes is currently increasing.

Therefore, much research has been conducted to improve ichtyosis by effectively removing dandruff-causing organisms. Particularly, zinc pyrithione and piroctone olamine have been proven to have an inhibitory effect on dandruff and pruritus, and thus have been widely used as antidandruff agents for hair care cosmetics. Zinc pyrithione may be problematic at a concentration of 1% or more since it is an irritant to the skin, and has a poor effect at a concentration of 0.01% or less. Preferably, zinc pyrithione is mixed at a concentration of 0.5%, and used. Zinc pyrithione has an advantage in that it is effective for treatment and improvement of ichtyosis since it has a good effect of suppressing hyperkeratosis of the scalp and a good antifungal effect. However, zinc pyrithione has problems in that it is difficult to uniformly disperse in a composition since it is insoluble in water and has a high specific gravity, and it is restricted to apply a high concentration of zinc pyrithione to hair care cosmetics since it particularly has problems about contact dermatitis to the skin (Nielsen, N. H., Allergic contact dermatitis caused by zinc pyrithione associated with pustular psoriasis. Am J Contact Dermat. 8, 170, 1997), environmental toxicity, and the like.

Meanwhile, as a water-soluble therapeutic agent for treating dandruff which compensates for the shortcomings of zinc pyrithione, piroctone olamine should be used at a concentration of 0.5 to 2.0% to exhibit a sufficient effect. In this case, such a component also tends to be regulated on its usage due to safety issues to the human body (Cosmetics and Toiletries, 102, 6, December, 1987). In addition, climbazole, sulfur, salicylic acid, tar, and the like have been used as antidandruff agents since they have an antibacterial effect on *Pityrosporum ovale* that is a microorganism present in the scalp.

From the foregoing, a combination therapy capable of compensating for an effect of the antidandruff agent while reducing a concentration of the antidandruff agent is required. In particular, although such a synthetic material has antibacterial activities, since consumers may have negative thoughts about the synthetic material in that it is not safe due to side effects in the skin, a natural substance-derived composition for preventing dandruff is required.

Meanwhile, although *Pityrosporum ovale* is often found in the scalps of ichtyosis patients, only suppressing this strain does not essentially mean improving ichtyosis. Accordingly, an issue where there is another cause of ichtyosis has been raised.

*Filobasidium* sp. is a fungus that belongs to the fungal class of Tremellomycetes. Among these, a family of Filobasidiaceae is divided into four species. This fungus has a characteristic of having no macroscopic basidiocarp observed with the naked eye unlike other Tremelloid species.

The fungus is the skin flora, and methods using the fungus to produce alcohol are disclosed in the prior art, but the fungus is still not identified as causing dandruff.

The present inventors have conducted research on the cause of dandruff, and found that there is a significant increase in the number of the fungus *Filobasidium* sp. in the scalps of ichtyosis patients, and that the fungus is identified as mainly causing dandruff. Therefore, they have contemplated that it is possible to prevent or treat ichtyosis by effectively removing these dandruff-causing organisms.

Accordingly, the present inventors have searched for materials which are environmentally and ecologically friendly, and having an effect of preventing and treating dandruff without causing safety issues to the human body, and confirmed that an extract derived from a fruit of *Gardenia jasminoides Ellis*, a fruit of *Poncirus trifoliata, Saururus chinensis, Benincasa hispida*, or a fruit of *Capsella bursa-pastoris* has an anti-*Filobasidium* effect. Therefore, the present invention has been completed based on these facts.

DISCLOSURE

Technical Problem

The present invention is designed to solve the problems of the prior art, and therefore it is an object of the present invention to provide an antimicrobial composition including a material derived from a natural substance. Specifically, it is an object of the present invention to provide an antimicrobial composition including a *Filobasidium* sp.-suppressing substance derived from a natural substance as an active ingredient. Especially, the composition is characterized in that it suppresses *Filobasidium* sp. which is a fungus that has been newly identified as causing dandruff.

However, a technical subject to be achieved by the present invention is not limited to the above-described subject, and other subjects which are not mentioned above will be clearly understood by those skilled in the art.

Technical Solution

According to an aspect of the present invention, there is provided an antimicrobial composition including a *Filobasidium*-suppressing substance derived from a natural substance.

According to one exemplary embodiment of the present invention, the natural substance may include at least one selected from the group consisting of a fruit of *Gardenia jasminoides Ellis*, a fruit of *Poncirus trifoliata, Saururus chinensis, Benincasa hispida*, and *Capsella bursa-pastoris*.

According to another exemplary embodiment of the present invention, the natural substance may be extracted with an organic solvent. The organic solvent may be at least one selected from the group consisting of chloroform, dichloromethane, ethyl acetate, butyl acetate, hexane, 1,3-butylene glycol, propylene glycol, benzyl alcohol, an ether, a ketone, an alcohol, etc. Here, the alcohol may be a C1-C6 alcohol. Preferably, an ethanol may be used as the alcohol. Acetone may be preferably used as the ketone. However, types of the solvent which may be used herein are not limited thereto.

According to still another exemplary embodiment of the present invention, the composition may be a composition for preventing or treating seborrhoeic dermatitis or dandruff.

According to still another exemplary embodiment of the present invention, the composition may be a hair cosmetic composition, and the hair cosmetic composition may include hair cosmetic compositions in the form of a soap, a shampoo, a hair conditioner, a hair tonic, a hair cream, a hair spray, and a hair mousse, but the present invention is not limited thereto.

According to yet another exemplary embodiment of the present invention, the composition may further include another anti-dandruff agent, and the other anti-dandruff agent may include zinc pyrithione, piroctone olamine, climbazole, tar, sulfur, and salicylic acid. However, types of the material which may be added thereto are not limited thereto.

Advantageous Effects

The composition according to one exemplary embodiment of the present invention includes a material derived from a natural substance as an active ingredient, and thus can provide an antimicrobial composition less repulsive to consumers, and particularly can be useful in reducing the content of materials whose safety is questionable and which have been used as the conventional antidandruff agents since the conventional antidandruff agents include the materials derived from natural substances. Further, since the composition can effectively suppress *Filobasidium* sp. which is a fungus that has been newly identified as causing dandruff, the composition is ultimately expected to be widely used to more effectively prevent and treat seborrhoeic dermatitis and dandruff.

MODES OF THE INVENTION

Figure 1:
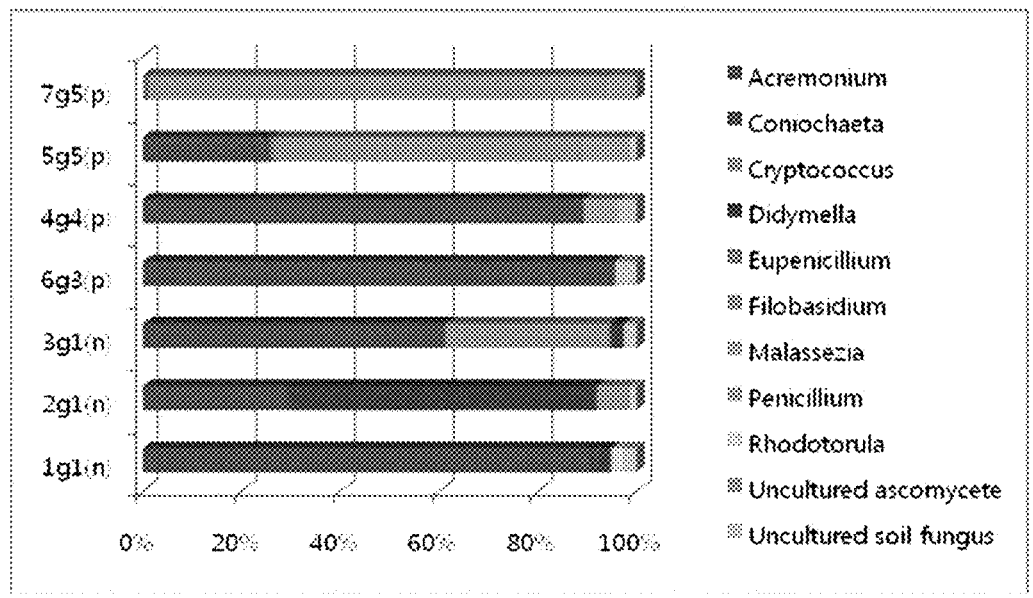
FIG. 1 is a graph illustrating that *Filobasidium floriforme* is superiorly found in grade V dandruff patients, as determined using a metagenomic assay.

The present inventors have conducted research on materials derived from natural substances effectively suppressing *Filobasidium* sp. that is a fungus that has been newly identified as causing dandruff. Therefore, the present invention has been completed based on these facts.

The composition according to one exemplary embodiment of the present invention may also include a component generally used to manufacture hair cosmetics, such as a surfactant, a base compound, an oil, an alcohol, a pigment, a perfume, a preservative, etc.

A shampoo composition for treating dandruff and preventing hair loss according to one exemplary embodiment of the present invention may be prepared into various formulations, which may be readily understood by those skilled in the related art. For example, the shampoo composition may be produced into formulations such as shampoos, rinses, hair tonics, pomades, hair treatments, hair lotions, etc.

Hereinafter, preparation methods, and a shampoo, a hair conditioner, a hair tonic, and a hair cream including an additive, which may be prepared by those skilled in the related art, will be described, as follows.

<Preparation of Shampoo>

A shampoo is prepared by mixing an anionic surfactant, a moisturizing agent, a hair-protecting component, water, etc. In the case of a shampoo formulation, 30% sodium lauryl sulfate, 30% polyoxyethylene sodium lauryl sulfate, coconut oil fatty acid diethanolamide, and propylene glycol are added to water. Thereafter, piroctone olamine that is a known component for preventing dandruff is added to the resulting mixture, dissolved by heating, and cooled. Zinc pyrithione, butylhydroxy toluene (BHT), a pigment, a paraoxybenzoate ester, a perfume, and citric acid are added to the mixture, and mixed with an extract according to one exemplary embodiment of the present invention, and cooled to prepare a shampoo.

<Preparation of Hair Conditioner>

In the case of a hair conditioner formulation, a cetanol, a self-emulsifying glyceryl monostearate, a paraoxybenzoate ester, 75% distearyldimethylammonium chloride, piroctone olamine that is a known component for preventing dandruff, and the like are added to water, dissolved by heating, and then cooled. Zinc pyrithione, BHT, a pigment, a perfume, and citric acid are added to the resulting mixture, and mixed with an extract according to one exemplary embodiment of the present invention to prepare a hair conditioner.

<Preparation of Hair Tonic>

In the case of a hair tonic formulation, a non-oily hair tonic is prepared by dissolving a disinfectant, an irritant, and the like in a 30 to 70% aqueous alcohol solution and adding a perfume to the resulting mixture, and an oily hair tonic is prepared by adding an oil, which is prepared by dissolving a disinfectant, an irritant, and a perfume, to a pure alcohol. Then, piroctone olamine that is a known component for preventing dandruff, and an extract according to one exemplary embodiment of the present invention are added to the mixtures to prepare hair tonics.

<Preparation of Hair Cream>

In the case of a hair cream formulation, beeswax, liquid paraffin, stearic acid, lanolin, a perfume, a preservative, and other several substances are blended, and piroctone olamine that is a known component for preventing dandruff, and an extract according to one exemplary embodiment of the present invention are added to the mixture to prepare a hair cream.

Hereinafter, preferred embodiments are provided to aid in understanding the present invention. However, it should be understood that detailed description provided herein is merely intended to provide a better understanding of the present invention, and is not intended to limit the scope of the present invention.

EXAMPLE 1

Analysis Using Metagenomic Assay for Identifying Dandruff-related Mycobiome 1-1. Collections of Samples and DNA Extraction To analyze a dandruff-causing organism, normal dandruff samples and dandruff patients' samples were collected from the dandruff patients coming to the department of dermatology of the Chung-Ang University College of Medicine under the approval of the Institutional Review Board (IRB) from the Chung-Ang University Medical Center.

Collection of the individual samples to analyze a mycobiome was carried out by rubbing scalps with a cotton swab soaked in an ST solution (0.15M NaCl with 0.1% Tween 20) in a DNA-free clean room. Seven collected samples of the dandruff patients were classified into grades I to V using a method by Park et al. (Korean J. Dermatol. 2009; 47: 875-883), depending on the conditions of the patients. The samples designated as 1g1, 2g1, and 3g1 were classified as having a normal scalp, or being dandruff-free, and the samples designated as 6g3, 4g4, 5g5, and 7g5 were classified as being patient samples. The collected samples were transferred to microcentrifuge tubes, and centrifuged for 10 minutes. Then, supernatants were discarded, and DNAs were extracted using a cetyltrimethylammonium bromide method, and then quantified using Infinite 200 NanoQuant.

Generally, primers for analyzing a mycobiome, NL1 (5'-GCATATCAATAAGCGGAGGAAAAG-3'; SEQ ID NO: 1) and NL4 (5'-GGTCCGTGTTTCAAGACGC-3'; SEQ ID NO: 2) were used to amplify a D1/D2 region of a 26S rRNA gene. To perform a large-scaled 454 pyrosequencing assay, a 10-base multiplex identifier (MID) sequence was added to all the 5'-termini of the primers. A reaction mixture including 5 to 25 ng of genomic DNA obtained from dandruff of each of the normal volunteers or patients, 0.4 mM primers, 0.2 mM dNTPs, 1.5 mM $MgCl_2$, a 2.0 U Hot Start Taq polymerase, and a 1.0×reaction buffer (Takara) was adjusted to a final volume of 25 µl, and subjected to a PCR reaction. A PCR amplification reaction was carried out in GeneAmp PCR system 9700 (Applied Biosystem): one denaturation cycle at 94° C. for 5 minutes, 30 amplification cycles at 94° C. for 30 seconds, at 55° C. for 30 seconds, and at 72° C. for 1 minute, and one final extension cycle at 72° C. for 10 minutes. PCR products were run in 1.2% agarose gel, stained with ethidium bromide (EtBr), and then checked using a UV transilluminator.

1-2. Large-scaled Sequencing Assay: 454 Pyrosequencing

The PCR products were obtained from the seven samples, a mixture of the PCR products was prepared from each of the samples to perform a 454 sequencing assay. The mixture of the PCR products was subjected to a GS-FLX Titanium sequencing assay, and quantified using a Pico Titer plate, and then subjected to a pyrosequencing assay. The sequenced DNA sequence was analyzed using a basic local alignment search tool (BLAST) from the US National Center for Biotechnology Information (NCBI; http://www.ncbi.nlm.nih.gov1).

1-3. Statistical Analysis

A factor analysis was used to analyze valid parameters from a total of sets of observed parameters. First, main components were checked together with general standard parameters having a cumulative dispersion of 70% or more. A constitutive matrix of deleted parameters and main selected parameters of factors loaded below 0.6 was estimated. Groups of the samples from the scalps of the dandruff patients and the scalps of the healthy volunteers were classified in consideration of a generalized linear model (GLM) using a final set of the selected parameters. When it is assumed that the parameter 't' is applied to the total number of frequencies in $g(\mu)=\alpha+\beta\times(a)$, the equation "$g(\mu)=\log(\mu/t)$" is satisfied, and the GLM is shown to comply with the equation (a). In this case, when the parameter 'β' was applied to the equation (a), the parameter 'β' was tested to be significant at the level of 5%.

From the analysis results, it was revealed that the DNA sequences having 10,735, 10,029, 12,119, 9,614, 9,092, 7,589, and 7,034 base pairs were obtained from the seven samples, respectively. In particular, the GLM analysis showed that *Filobasidium floriforme* was superiorly found in the grade V dandruff patients, and thus expected to be a dandruff-related fungus (see Table 1 and FIG. 1).

TABLE 1

| Classification level | Name | % average (normal) | % average (patient) | Estimate | Standard error | p-value |
|---|---|---|---|---|---|---|
| Phylum | Ascomycota | 82.57 | 61.30 | 0.2979 | 0.0093 | <0.0001 |
| | Basidiomycota | 13.12 | 35.70 | −1.0011 | 0.0178 | <0.0001 |
| | Uncultured_fungus | 4.31 | 3.00 | 0.3627 | 0.0413 | <0.0001 |
| Genus | Acremonium_spp. | 61.77 | 57.91 | 0.042 | 0.0102 | <0.0001 |
| | Coniochaeta_velutina | 0.49 | 0.00 | 5.0654 | 1.0032 | <0.0001 |
| | Cryptococcus spp. | 12.31 | 0.26 | 3.8312 | 0.109 | <0.0001 |
| | Didymella spp. | 20.22 | 0.05 | 6.0094 | 0.2503 | <0.0001 |
| | Eupenicillium spp. | 0.01 | 0.04 | −1.8498 | 0.7596 | 0.0149 |
| | Filobasidium floriforme | 0.20 | 33.85 | −5.1703 | 0.1274 | <0.0001 |
| | Malassezia spp. | 0.07 | 1.91 | −3.376 | 0.2218 | <0.0001 |
| | Penicillium spp. | 0.05 | 3.44 | −4.3043 | 0.2599 | <0.0001 |
| | Rhodotorula spp. | 0.84 | 0.05 | 2.8899 | 0.2654 | <0.0001 |
| | Uncultured ascomycete | 1.92 | 0.02 | 4.3478 | 0.3559 | <0.0001 |
| | Uncultured soil fungus | 2.14 | 2.47 | −0.1667 | 0.0521 | 0.0014 |

EXAMPLE 2

Preparation of Extract of Natural Substance

A fruit of *Gardenia jasminoides Ellis*, a fruit of *Poncirus trifoliata*, a root of *Rubus coreanus*. Miq., *Camellia sinensis*, *Houttuynia cordata*, *Ulmus macrocarpa*, *Poria cocos Wolf*, *Saururus chinensis*, *Dictamnus dasycarpus Turcz.*, *Benincasa hispida*, all of which were dried over 1,000 ml of 99.5% acetone and 1,000 ml of 95% ethanol and finely cut in the form of medicine, and *Capsella bursa-pastoris* (purchased from the Kyeongdong medicine markets) were mixed at a content of 100 g, respectively, and then kept at 24° C. for 24 hours to obtain an extract. Thereafter, the extract was filtered through a filter paper (Whatman) to be separated into sludge and a solution. The separated solution was quadruply concentrated at 42° C. using an evaporator (Heidolph vv 2000) so as to remove acetone from the solution.

EXAMPLE 3

Measurement of Anti-*Filobasidium* Fungal Activity of Natural Substance Extract

The anti-*Filobasidium* activities of the acetone and ethanol extracts prepared in Example 2 were measured. As a reference strain, *Filobasidium floriforme* KCTC 7988$^T$ was purchased from the Korean Collection for Type Cultures (KCTC) from the Biological Resource Center (BRC) at the Korea Research Institute of Bioscience & Biotechnology, and used in this experiment.

A single colony of each of test strains was seeded in a 200 ml flask containing 10 ml of a nutrient medium (Modified Dixon's agar), and cultured for 12 hours while stirring at 37° C. The culture broth was inoculated in a 200 ml flask containing 10 ml of a nutrient medium at an initial optical density (O.D.) of 0.1, and subcultured for 7 hours. The culture broth of each of the test strains activated by the above-described method was adjusted so that the number of the test strains per plate was $2.0 \times 10^8$, and poured in a 1,000 mm Petri dish together with 13 ml of a nutrient agar broth which was not set hard at 60° C., and then sufficiently set hard. Thereafter, 10 mm paper disks (Toyo Roshi Kaisha, Ltd, Japan) which were dried at 56° C. for 24 hours in an incubator to completely remove moisture were put on the plate, and an acetone extract of the fruit of *Gardenia jasminoides Ellis* prepared in Example 1 was injected at a concentration of 100 µl into the respective paper disks. The plate was incubated at 37° C. for 12 hours in an incubator, and formed fungal growth inhibition zones, that is, clear zones were checked. Then, the diameters of the clear zones were measured using Vernier calipers.

Figure 2:
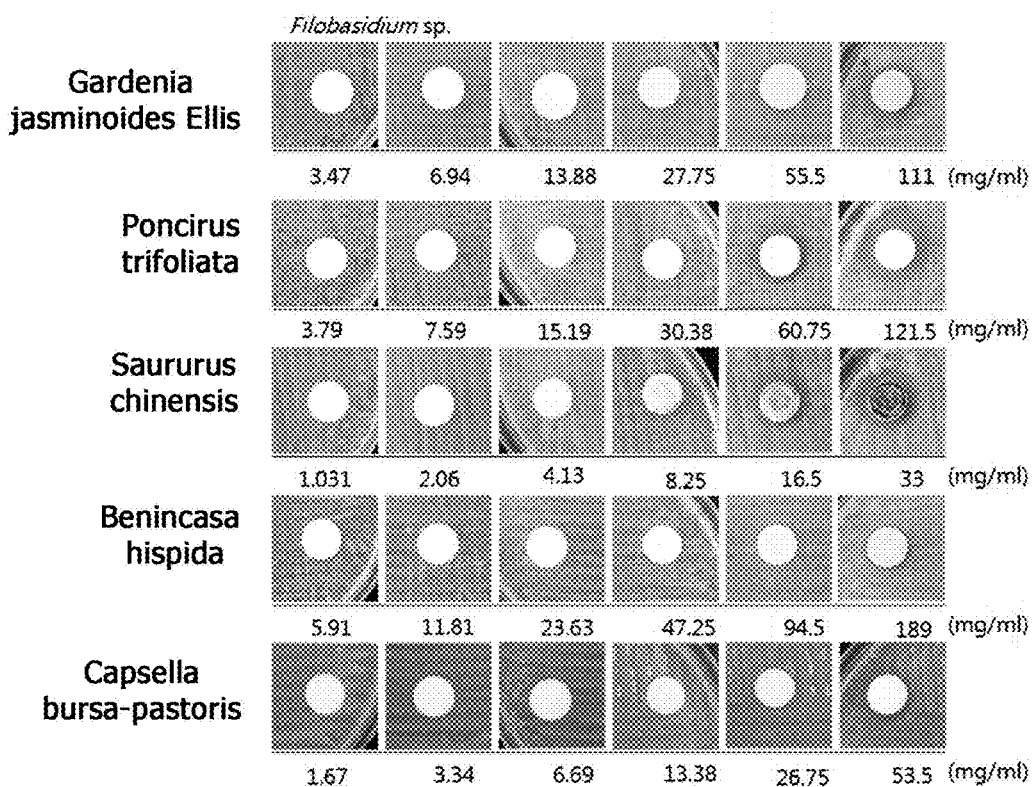
FIG. 2 is a diagram showing fungal growth inhibition zones, that is, clear zones formed when an acetone extract of a fruit of *Gardenia jasminoides Ellis*, an acetone extract of a fruit of *Poncirus trifoliata*, an acetone extract of *Saururus chinensis*, an ethanol extract of *Benincasa hispida*, and an ethanol extract of *Capsella bursa-pastoris* are added, respectively.

From the experimental results, it could be seen that the acetone extracts of the fruits of *Gardenia jasminoides Ellis* and *Poncirus trifoliata*, and the ethanol extracts of *Saururus chinensis*, *Benincasa hispida*, and *Capsella bursa-pastoris* had an antifungal effect against the fungus *Filobasidium* sp. (see Tables 2 to 6 and FIG. 2).

In the Tables, the term 'N.D.' represents 'not detected,' and the number represents a fungal growth inhibition zone including a diameter of a paper disk (10 mm).

Table 2 lists the experimental results of the acetone extract of *Gardenia jasminoides Ellis*, Table 3 lists the experimental results of the acetone extract of *Poncirus trifoliata*, Table 4 lists the experimental results of the ethanol extract of *Saururus chinensis*, Table 5 lists the experimental results of the ethanol extract of *Benincasa hispida*, and Table 6 lists the experimental results of the ethanol extract of *Capsella bursa-pastoris*.

TABLE 2

| Fungus | Concentration of extract | | | | | |
|---|---|---|---|---|---|---|
| | 111.00 | 55.50 | 27.80 | 13.90 | 6.90 | 3.50 |
| *Filobasidium* sp. | 14 | N.D. | N.D. | N.D. | N.D. | N.D. |

(concentration units: mg/ml; activity units: mm)

TABLE 3

| | Concentration of extract | | | | | |
|---|---|---|---|---|---|---|
| Fungus | 121.50 | 60.75 | 30.38 | 15.19 | 7.59 | 3.80 |
| *Filobasidium* sp. | 19.00 | 14.00 | N.D. | N.D. | N.D. | N.D. |

(concentration units: mg/ml; activity units: mm)

TABLE 4

| | Concentration of extract | | | | | |
|---|---|---|---|---|---|---|
| Fungus | 33.00 | 16.50 | 8.25 | 4.13 | 2.06 | 1.03 |
| *Filobasidium* sp. | 16 | N.D. | N.D. | N.D. | N.D. | N.D. |

(concentration units: mg/ml; activity units: mm)

TABLE 5

| | Concentration of extract | | | | | |
|---|---|---|---|---|---|---|
| Fungus | 189.00 | 94.50 | 47.25 | 23.63 | 11.81 | 5.91 |
| *Filobasidium* sp. | 12.00 | N.D. | N.D. | N.D. | N.D. | N.D. |

(concentration units: mg/ml; activity units: mm)

TABLE 6

| | Concentration of extract | | | | | |
|---|---|---|---|---|---|---|
| Fungus | 53.50 | 26.75 | 13.38 | 6.69 | 3.34 | 1.67 |
| *Filobasidium* sp. | 14 | N.D. | N.D. | N.D. | N.D. | N.D. |

(concentration units: mg/ml; activity units: mm)

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

INDUSTRIAL APPLICABILITY

The composition according to one exemplary embodiment of the present invention includes a material derived from a natural substance as an active ingredient, and thus can provide an antimicrobial composition less repulsive to consumers, and particularly can be useful in reducing the content of materials whose safety is questionable and which have been used as the conventional antidandruff agents since the conventional antidandruff agents include the materials derived from natural substances. Further, since the composition can effectively suppress *Filobasidium* sp. which is a fungus that has been newly identified as causing dandruff, the composition is ultimately expected to be widely used to more effectively prevent and treat seborrhoeic dermatitis and dandruff.

The invention claimed is:

1. A method of treating dandruff, the method comprising: applying, to scalp of a subject in need of treating dandruff, an effective amount of a composition comprising an organic solvent-based extract from a fruit of *Poncirus trifoliata* and further comprising an organic solvent-based extract from at least one additional plant material selected from the group consisting of *Saururus chinensis, Benincasa hispida* and *Capsella bursa-pastoris*.

2. The method of claim 1, wherein the organic solvent-based extract from a fruit of *Poncirus trifoliata* is an ethanol-based extract.

3. The method of claim 1, wherein the organic solvent for the organic solvent-based extract comprises at least one selected from the group consisting of chloroform, dichloromethane, ethyl acetate, butyl acetate, hexane, 1,3-butylene glycol, propylene glycol, benzyl alcohol, an ether, a ketone, and an alcohol.

4. The method of claim 3, wherein the alcohol is a C1-C6 alcohol, and the ketone is acetone.

5. The method of claim 4, wherein the alcohol is ethanol.

6. The method of claim 1, wherein the composition further comprises at least one selected from the group consisting of zinc pyrithione, piroctone olamine, climbazole, tar, sulfur, and salicylic acid.

7. The method of claim 1, wherein the composition comprises the organic solvent-based extract from a fruit of *Poncirus trifoliata* and the organic solvent-based extract from *Saururus chinensis*.

8. The method of claim 1, wherein the composition comprises the organic solvent-based extract from a fruit of *Poncirus trifoliata* and the organic solvent-based extract from *Benincasa hispida*.

9. The method of claim 1, wherein the composition comprises the organic solvent-based extract from a fruit of *Poncirus trifoliata* and the organic solvent-based extract from *Capsella bursa-pastoris*.

* * * * *